(12) United States Patent
Matalon

(10) Patent No.: US 8,252,596 B2
(45) Date of Patent: Aug. 28, 2012

(54) METHODS AND MATERIALS FOR TREATING CONDITIONS ASSOCIATED WITH METABOLIC DISORDERS

(75) Inventor: Reuben Matalon, Houston, TX (US)

(73) Assignee: PreKUlab Ltd., Korsor (DK)

( * ) Notice: Subject to any disclaimer, the term of this patent is extended or adjusted under 35 U.S.C. 154(b) by 0 days.

(21) Appl. No.: 12/805,554

(22) Filed: Aug. 5, 2010

(65) Prior Publication Data

US 2011/0038932 A1 Feb. 17, 2011

Related U.S. Application Data

(62) Division of application No. 10/826,112, filed on Apr. 17, 2004.

(60) Provisional application No. 60/490,473, filed on Jul. 28, 2003.

(51) Int. Cl.
*G01N 33/00* (2006.01)
(52) U.S. Cl. .............................. 436/89; 436/90; 514/183
(58) Field of Classification Search .................. None
See application file for complete search history.

(56) References Cited

U.S. PATENT DOCUMENTS 5,411,757 A * 5/1995 Buist et al. .................... 426/656

FOREIGN PATENT DOCUMENTS

DE 4037447 * 2/1992

OTHER PUBLICATIONS

English Translation of German Patent DE 4037447, Inventor Wachtel et al., publication date 1992, pp. 1-19.*
Pietz, J. et al., "Large neutral amino acids block phenylalanine transport into brain tissue in patients with phenylketonuria," J. Clin. Invest 103:1169-1178 (1999).
Koch, R. et al., "Large neutral amino acid therapy and phenylketonuria: a promising approach to treatment," Molecular Genetics and Metabolism 79 (2003) 110-113.
Matalon, R. et al., "Large neutral amino acids in the treatment of phenylketonuria (PKU)," J Inherit Metab Dis (2006) 29:732-738.
Matalon, R. et al., "Double blind placebo control trial of large neutral amino acids in treatment of PKU: Effect on blood phenylalanine," J Inherit Metab Dis (2007) 30:153-158.
Schindeler, S. et al., "The eVects of large neutral amino acid supplements in PKU: An MRS and neuropsychological study," Molecular Genetics and Metabolism 91 (2007) 48-54.

* cited by examiner

*Primary Examiner* — Jeffrey S. Lundgren
*Assistant Examiner* — Meghan Finn
(74) *Attorney, Agent, or Firm* — Faegre Baker Daniels LLP

(57) ABSTRACT

Disclosed are methods for treating a subject suffering from phenylketonuria and/or phenylalanemia. The methods include, in part, enterally administering to the subject a LNAA supplement in which the weight ratio of Leu to Val is greater than 2:1; in which the weight ratio of Leu to iLeu is greater than 3:1; or which includes one or more LNAAs and which further includes Lys. LNAA supplements are also disclosed. Also disclosed are methods for treating a subject suffering from a condition involving a metabolic disorder involving the metabolism of a first amino acid X. The method includes enterally administering to the subject a composition which (i) is substantially free from the first amino acid X and (ii) which includes a second amino acid Y that competes with amino acid X at a gastrointestinal tract transporter.

26 Claims, No Drawings

METHODS AND MATERIALS FOR TREATING CONDITIONS ASSOCIATED WITH METABOLIC DISORDERS

CROSS-REFERENCE TO RELATED APPLICATION

This is a divisional application of U.S. patent application Ser. No. 10/826,112, filed Apr. 17, 2004, which claims the benefit of U.S. Provisional Patent Application Ser. No. 60/490,473 filed Jul. 28, 2003, both hereby incorporated in their entirety by reference.

FIELD OF THE INVENTION

The subject invention is directed, generally, to methods and materials for treating conditions associated with metabolic disorders and, more particularly, to methods and materials for treating conditions associated with metabolic disorders of particular amino acids.

BACKGROUND OF THE INVENTION

A number of conditions which afflict humans and other animals are attributable to disorders in metabolizing particular amino acids. In many of these conditions, treatment involves restricting the dietary intake of the particular amino acid or amino acids associated with the condition. However, therapies based on dietary restriction requires patient compliance and also requires that the patient know whether a particular food contains the particular amino acid or amino acids associated with the condition.

For example, phenylketonuria ("PKU") is hyperaminoacidemia of phenylalanine (Phe) associated with an inborn error of phenylalanine metabolism, mutation of the gene encoding phenylalanine 4-hydroxylase ("PAH"), which converts phenylalanine to tyrosine. In some cases, an additional metabolic defect occurs in the synthetic pathway of either dihydropteridine or tetrahydrobiopterin ("BH4"), PAH co-factors, contributing further to the hyperphenylalaninemia ("HPA"). Whereas a normal plasma Phe level is approximately 0.05 mM (Pardridge, "Blood-Brain Barrier Amino Acid Transport: Clinical Implications," chapter 6 in *Inborn Errors of Metabolism in Humans*, Cockburn et al., eds, Lancaster, England: MTP Press Ltd. (1980) ("Pardridge")), untreated "classic" PKU patients have plasma Phe levels above 1 mM (e.g., plasma Phe levels of from about 1 mM to about 2.5 mM or more), and, although treatment with a low-Phe diet has a goal of reducing plasma Phe to below 0.3 mM, this is difficult to attain due to dietary compliance problems. In the US, 1 in 10,000 babies are born with PKU.

The excessive levels of plasma phenylalanine observed in PKU combined with the relatively high affinity of Phe for binding sites on carrier protein of the neutral amino acid transport system in the blood-brain barrier ("BBB") leads to (i) accumulation of Phe and its neurotoxic metabolites (e.g., phenylpyruvate, phenylacetate, phenyllactate) in the brain and (ii) depressed levels of non-Phe neutral amino acids entering the brain, resulting in disturbed brain development and function, since key cerebral pathways of metabolism (e.g., synthesis of neurotransmitters) require precursor amino acids, such as tyrosine. This depression is pronounced for tyrosine, which is low in the plasma supply due to the PKU metabolic error in the enzyme responsible for converting phenylalanine to tyrosine. Current thought is that the neurological deficits of PKU are due predominantly to the depression of levels of non-Phe neutral amino acids entering the brain (Kaufman, "Some Facts Relevant to a Consideration of a Possible Alternative Treatment for Classical Phenylketonuria," *J. Inher. Metab. Dis.*, 21 (supplement 3):4-19 (1998) ("Kaufman")).

Although a diet low in phenylalanine can reduce plasma Phe levels in "classic" PKU below 0.3 mM and ameliorate the mental retardation associated with untreated PKU, dietary compliance becomes problematic as PKU patients reach adolescence, leading to a rise in plasma Phe levels and to both loss in intelligence and white matter changes in the brain. Nutritional deficiencies can also result from Phe-restricted diets. Alternative treatments have thus been developed. For example, to overcome suspected depletion of the neurotransmitters dopamine and serotonin, PKU patients have been treated with the neurotransmitter precursors tyrosine and tryptophan (Lou, "Large Doses of Tryptophan and Tyrosine as Potential Therapeutic Alternative to Dietary Phenylalanine Restriction in Phenylketonuria," *Lancet*, 2:150-151 (1983)). To reduce influx of Phe into the brain, a supplement of branched chain neutral amino acids containing valine, isoleucine, and leucine, was administered to older PKU patients (Berry et al, "Valine, Isoleucine and Leucine. A New Treatment for Phenylketonuria," *Am. J. Dis. Child.*, 144:539-543 (1990) ("Berry")), who reported significant improvement in behavioral deficits. In Kaufman, it was proposed that the addition of the neurotransmitter precursors, tyrosine and tryptophan to Berry's supplement, should lead to further improvement. However, efficacy of these dietary amino acid supplement treatments has been controversial.

Tyrosinemia is another example of a condition that is attributable to a disorder in metabolizing particular amino acids. More particularly, tyrosinemia is a disorder caused by a defect in the terminal enzyme of the tyrosine metabolic pathway, leading to accumulation of fumarylacetoacetate, which converts to succinylacetone, which accumulates and is toxic to the liver. Tyrosinemia is associated with liver failure, liver diseases, and hepatocarcinoma. Liver transplantation can restore normal enzyme activity to the tyrosine metabolic pathway and is utilized in advanced cases. However this is a difficult and expensive therapy. Another currently employed therapy for tyrosinemia includes a two-fold approach: (i) use of a new inhibitor of tyrosine hydroxylase, NTBC ((2-(2-nitro-4-trifluoromethylbenzoyl)-1,3-cyclohexanedione), which prevents formation of succinylacetone; and (ii) a diet low in both tyrosine and phenylalanine to manage the amount of tyrosine which must be metabolized. However, safety issues regarding NTBC are unanswered to date, and dietary restriction of tyrosine and phenylalanine is dependent on patient knowledge and compliance, which, as mentioned above, can be problematic, especially in adolescents and adults.

Alkaptonuria is another example of a condition that is attributable to a disorder in metabolizing particular amino acids. Current therapies include restricting dietary intake of phenylalanine and tyrosine to reduce accumulation of the metabolite, homogentisic acid. Some patients take NTBC and vitamin C to reduce homogentisic acid aggregates. However, safety issues regarding NTBC are unanswered to date, and dietary restriction of tyrosine and phenylalanine is dependent on patient knowledge and compliance, which, as mentioned above, can be problematic.

Homocystinuria is another example of a condition that is attributable to a disorder in metabolizing particular amino acids. Patients with this condition frequently follow a methionine restricted diet. However, dietary restriction of methionine is dependent on patient knowledge and compliance, which, as mentioned above, can be problematic.

A number of conditions are attributable to metabolic disorders affecting the metabolism of the branched chain amino acids ("BCAAs"), such as leucine, isoleucine, and valine. Leucine, isoleucine, and valine are essential amino acids which must be obtained from dietary protein. A defect in one step of a multistep metabolic pathway which converts the BCAAs to energy, results in accumulation of an intermediate metabolite of the BCAA to toxic levels, causing disease. This is a large group of diseases that includes, for example, maple syrup urine disease ("MSUD"), isovaleric acidemia, methylmalonic acidemia, and propionic acidemia. These diseases are treated with special dietary formulas low in the BCAA having the metabolic defect. However, as discussed above, successful management of such diseases and conditions by dietary restriction of a particular amino acid or a particular set of amino acids is dependent on patient knowledge and compliance, which can be problematic.

In view of the above, there is a need for methods and materials for treating conditions, such as phenylketonuria, that are attributable to a disorder in metabolizing particular amino acids, and the present invention, in part, is directed to meeting this need.

SUMMARY OF THE INVENTION

The present invention relates to a method for treating a subject suffering from phenylketonuria and/or phenylalanemia. This method includes enterally administering to the subject a LNAA supplement in which the weight ratio of Leu to Val is greater than 2:1.

The present invention also relates to another method for treating a subject suffering from phenylketonuria and/or phenylalanemia. This method includes enterally administering to the subject a LNAA supplement in which the weight ratio of Leu to iLeu is greater than 3:1.

The present invention also relates to another method for treating a subject suffering from phenylketonuria and/or phenylalanemia. This method includes enterally administering to the subject a LNAA supplement which comprises one or more LNAAs and which further comprises Lys.

The present invention also relates to a LNAA supplement which includes Leu and Val and in which the weight ratio of Leu to Val is greater than 2:1.

The present invention also relates to a LNAA supplement which includes Leu and iLeu and in which the weight ratio of Leu to iLeu is greater than 3:1.

The present invention also relates to a LNAA supplement which includes one or more LNAAs and further includes Lys.

The present invention also relates to a LNAA supplement which includes, per 600 mg of LNAA supplement, from about 100 mg to about 290 mg of Tyr; from about 30 mg to about 90 mg of Trp; from about 25 mg to about 75 mg of Met; from about 15 mg to about 45 mg of iLeu; from about 15 mg to about 50 mg of Threo; from about 15 mg to about 50 mg of Val; from about 40 mg to about 200 mg of Leu; from about 15 mg to about 45 mg of His; and from about 15 mg to about 50 mg of Arg.

The present invention also relates to a method for treating a subject suffering from a condition involving a metabolic disorder involving the metabolism of a first amino acid X. The method includes enterally administering to the subject a composition which (i) is substantially free from the first amino acid X and (ii) which includes a second amino acid Y that competes with amino acid X at a gastrointestinal tract transporter. As one skilled in the art will appreciate, the composition can further include (i.e., in addition to second amino acid Y) other components, such as other amino acids (e.g., one or more other amino acids which compete with amino acid X at a gastrointestinal tract transporter).

DETAILED DESCRIPTION OF THE INVENTION

As used herein, "LNAA supplement" is meant to refer to any composition which includes, at a minimum, one or more large neutral amino acids, such as Phe, Leu, Tyr, Trp, Met, iLeu, Val, and Threo. The LNAA supplement can optionally include other components, such as basic amino acids (e.g., Arg, His, Lys, etc.) and/or other amino acids, vitamins, minerals, binders, diluents, dispersing agents, and other excipients. Illustratively, the LNAA supplement can include one, two, three, four, five, six, or more than six large neutral amino acids. The LNAA supplement can be substantially free from one or more specified amino acids, as in the case, for example, where the LNAA supplement is substantially free from amino acid Z. As used in this context, an LNAA supplement is to be deemed to be substantially free from amino acid Z when amino acid Z is present in an amount that is less than 10% (e.g., less than about 9%, less than about 8%, less than about 7%, less than about 6%, less than about 5%, less than about 4%, less than about 3%, less than about 2%, and/or less than about 1%), by weight, of the total weight of all of the large neutral amino acids present in the LNAA supplement.

"Treating", as used herein, is meant to refer to treatment of the direct or indirect cause of a condition; to treatment of a condition's symptoms; or to both.

"Subject", as used herein, is meant to refer to any animal, such as any mammal, e.g., mice rats, cats, rabbits, dogs, pigs, horses, cows, and primates, such as humans. Illustratively, "subject", as used herein, is meant to include human infants, human children, human adolescents, human adults, male humans, female humans, humans who are less than about 2 years of age, humans who are between about 2 years of age and 5 years of age, humans who are between about 5 and about 10 years of age, humans who are between about 10 and about 18 years of age, humans who are between about 18 and about 30 years of age, humans who are between about 30 and about 40 years of age, humans who are between about 40 and about 50 years of age, humans who are between about 50 and about 60 years of age, humans who are over about 60 years of age, humans suffering from phenylketonuria, humans not suffering from phenylketonuria, humans suffering from phenylalanemia, humans not suffering from phenylalanemia, humans suffering from tyrosinemia, humans not suffering from tyrosinemia, humans suffering from alkaptonuria, humans not suffering from alkaptonuria, humans suffering from homocystinuria, humans not suffering from homocystinuria, humans suffering from maple syrup urine disease, humans not suffering from maple syrup urine disease, humans suffering from isovaleric acidemia, humans not suffering from isovaleric acidemia, humans suffering from methylmalonic acidemia, humans not suffering from methylmalonic acidemia, humans suffering from propionic acidemia, and/or humans not suffering from methylmalonic acidemia.

As used herein, "enteral administration" of a substance is meant to refer to any administration which delivers the substance to one or more portions of the gastrointestinal ("GI") tract, such as the stomach, the small intestine, and the large intestine. For example, enteral administration can be carried out orally, for example, by swallowing a tablet, capsule, or other solid dosage form or by swallowing a liquid solution or suspension. Additionally or alternatively, enteral administration can be carried out by feeding tube, by gavage, or by other common methods of enteral administration.

One aspect of the present invention relates to a method for treating a subject suffering from phenylketonuria and/or phenylalanemia. This method includes enterally administering to the subject a LNAA supplement in which the weight ratio of Leu to Val is greater than 2:1, such as greater than about 2.2:1, greater than about 2.5:1, greater than about 2.8:1, greater than about 3:1, greater than about 3.2:1, greater than about 3.5:1, greater than about 3.8:1, greater than about 4:1, greater than about 4.2:1, greater than about 4.5:1, greater than about 4.8:1, greater than about 5:1, greater than about 5.2:1, greater than about 5.5:1, greater than about 5.8:1, greater than about 6:1, and/or greater than about 6.2:1. The LNAA supplement can be substantially free from phenylalanine. The LNAA supplement can also include Arg but no His or Lys; it can also include His but no Arg or Lys; it can also include Lys but no His or Arg; it can also include Arg and Lys but no His; it can also include Arg and His but no Lys; it can also include His and Lys but no Arg; or it can also include His, Arg, and Lys.

Another aspect of the present invention relates to a method for treating a subject suffering from phenylketonuria and/or phenylalanemia. This method includes enterally administering to the subject a LNAA supplement in which the weight ratio of Leu to iLeu is greater than 3:1, such as greater than about 3.2:1, greater than about 3.5:1, greater than about 3.8:1, greater than about 4:1, greater than about 4.2:1, greater than about 4.5:1, greater than about 4.8:1, greater than about 5:1, greater than about 5.2:1, greater than about 5.5:1, greater than about 5.8:1, greater than about 6:1, and/or greater than about 6.2:1. This LNAA supplement can be one in which the weight ratio of Leu to Val in the LNAA supplement is greater than 2:1, such as in the case where the weight ratio of Leu to Val is greater than about 2.2:1, greater than about 2.5:1, greater than about 2.8:1, greater than about 3:1, greater than about 3.2:1, greater than about 3.5:1, greater than about 3.8:1, greater than about 4:1, greater than about 4.2:1, greater than about 4.5:1, greater than about 4.8:1, greater than about 5:1, greater than about 5.2:1, greater than about 5.5:1, greater than about 5.8:1, greater than about 6:1, and/or greater than about 6.2:1. The LNAA supplement can be substantially free from phenylalanine. The LNAA supplement can also include Arg but no His or Lys; it can also include His but no Arg or Lys; it can also include Lys but no His or Arg; it can also include Arg and Lys but no His; it can also include Arg and His but no Lys; it can also include His and Lys but no Arg; or it can also include His, Arg, and Lys.

Another aspect of the present invention relates to a method for treating a subject suffering from phenylketonuria and/or phenylalanemia. This method includes enterally administering to the subject a LNAA supplement which includes one or more LNAAs and which further includes Lys.

Illustratively, the LNAA supplement of this aspect of the present invention can include Leu and Lys; or the LNAA supplement can include Leu and iLeu and Lys, such as where the LNAA supplement includes Leu and iLeu and Lys and where the weight ratio of Leu to iLeu in the LNAA supplement is greater than about 0.5:1, greater than about 1:1, greater than 1:1, greater than about 1.5:1, greater than about 2:1, greater than about 2:1, greater than about 2.5:1, greater than about 3:1, greater than 3:1, greater than about 3.2:1, greater than about 3.5:1, greater than about 3.8:1, greater than about 4:1, greater than about 4.2:1, greater than about 4.5:1, greater than about 4.8:1, greater than about 5:1, greater than about 5.2:1, greater than about 5.5:1, greater than about 5.8:1, greater than about 6:1, and/or greater than about 6.2:1.

As further illustration, the LNAA supplement of this aspect of the present invention can include Leu and Lys; or the LNAA supplement can include Leu and Val and Lys, such as where the LNAA supplement includes Leu and Val and Lys and where the weight ratio of Leu to Val in the LNAA supplement is greater than about 0.5:1, greater than about 1:1, greater than 1:1, greater than about 1.5:1, greater than about 2:1, greater than about 2:1, greater than about 2.5:1, greater than about 3:1, greater than about 3:1, greater than about 3.2:1, greater than about 3.5:1, greater than about 3.8:1, greater than about 4:1, greater than about 4.2:1, greater than about 4.5:1, greater than about 4.8:1, greater than about 5:1, greater than about 5.2:1, greater than about 5.5:1, greater than about 5.8:1, greater than about 6:1, and/or greater than about 6.2:1.

As yet further illustration, the LNAA supplement of this aspect of the present invention can be one which includes Leu; in which the weight ratio of Leu to iLeu in the LNAA supplement is greater than about 0.5:1; and in which the weight ratio of Leu to Val in the LNAA supplement is greater than about 0.5:1. For example, the LNAA supplement of this aspect of the present invention can be one which includes Leu; in which the weight ratio of Leu to iLeu in the LNAA supplement is greater than 3:1; and in which the weight ratio of Leu to Val in the LNAA supplement is greater than about 0.5:1. As another example, the LNAA supplement of this aspect of the present invention can be one which includes Leu; in which the weight ratio of Leu to iLeu in the LNAA supplement is greater than about 0.5:1; and in which the weight ratio of Leu to Val in the LNAA supplement is greater than 2:1. As yet another example, the LNAA supplement of this aspect of the present invention can be one which includes Leu; in which the weight ratio of Leu to iLeu in the LNAA supplement is greater than 3:1; and in which the weight ratio of Leu to Val in the LNAA supplement is greater than 2:1.

As one skilled in the art will appreciate, the methods of this aspect of the present invention (i.e., by enterally administering to the subject a LNAA supplement which includes one or more LNAAs and which further includes Lys) can be practiced with an LNAA supplement that is substantially free from phenylalanine. Additionally or alternatively, the LNAA supplement can further include Arg and/or His or the LNAA supplement can be substantially free from Arg and/or His.

In one particular embodiment of this aspect of the present invention, the LNAA supplement includes, per 500 mg of LNAA supplement:

from about 100 mg to about 290 mg of Tyr;
from about 25 mg to about 75 mg of Trp;
from about 15 mg to about 50 mg of Met;
from about 15 mg to about 55 mg of iLeu;
from about 15 mg to about 50 mg of Threo;
from about 15 mg to about 55 mg of Val;
from about 15 mg to about 200 mg of Leu;
from about 10 mg to about 30 mg of His; and
from about 5 mg to about 200 mg of Lys.

As one skilled in the art will appreciate, the amounts of each amino acid present in this LNAA supplement can be varied within the stated limits. Thus, for example, the LNAA supplement can include, per 500 mg of LNAA supplement, from about 10 mg to about 30 mg of Lys. Moreover, as one skilled in the art will also appreciate, this LNAA supplement can optionally include one or more other amino acids not mentioned above, or the LNAA supplement can be substantially free of one or more other amino acids not mentioned above. Thus, for example, this LNAA supplement can optionally include Arg, or it can be substantially free from arginine; and/or it can be substantially free from phenylalanine.

Yet another aspect of the present invention relates to a method for treating a subject suffering from phenylketonuria and/or phenylalanemia. This method includes enterally administering to the subject a LNAA supplement which includes, per 600 mg of LNAA supplement:

from about 100 mg to about 290 mg of Tyr;
from about 30 mg to about 90 mg of Trp;
from about 25 mg to about 75 mg of Met;
from about 15 mg to about 45 mg of iLeu;
from about 15 mg to about 50 mg of Threo;
from about 15 mg to about 50 mg of Val;
from about 40 mg to about 200 mg of Leu;
from about 15 mg to about 45 mg of His; and
from about 15 mg to about 50 mg of Arg.

As one skilled in the art will appreciate, the amounts of each amino acid present in this LNAA supplement can be varied within the stated limits. Moreover, as one skilled in the art will also appreciate, the LNAA supplement of this aspect of the present invention can optionally include one or more other amino acids not mentioned above, or the LNAA supplement of this aspect of the present invention can be substantially free of one or more other amino acids not mentioned above. Thus, for example, the LNAA supplement of this aspect of the present invention can optionally include Lys (e.g., from about 5 mg to about 200 mg of Lys per 600 mg of LNAA supplement, or it can be substantially free from Lys; and/or it can be substantially free from phenylalanine.

The methods of the various aspects of the present invention discussed above can be carried out by any suitable form of enteral administration of the LNAA supplement to the subject. It will be appreciated that the actual preferred amount of LNAA supplement to be administered according to the present invention will vary according to the particular large neutral amino acid or acids that are present in the LNAA supplement, the nature of the other components present in the LNAA supplement, and the form of enteral of administration. Many factors that may modify the action of the LNAA supplement (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests, such as those described in the examples which follow. Briefly, dosing can be based on the level of plasma phenylalanine. For example, dosing can be based on the level of plasma phenylalanine at 0, 3, and/or 6 hours following administration of the LNAA supplement.

Illustratively, the LNAA supplement can be administered in a single oral dose of from about 0.1 g to about 10 g per kg of the subject's body weight substantially at mealtime. As used herein, "substantially at mealtime" is meant to refer to the period of time from about 4 hours before mealtime to about 1 hour after mealtime, such as from about 4 hours before mealtime to about mealtime, from about 3 hours before mealtime to about mealtime, from about 2 hours before mealtime to about mealtime, from about 1 hour before mealtime to about mealtime, and/or from about 0.5 hours before mealtime to about mealtime. For example, the LNAA supplement can be administered in a single oral dose of from about 0.2 g to about 5 g per kg, such as from about 0.3 g to about 3 g per kg, from about 0.4 g to about 2 g per kg, from about 0.5 g to about 1 g per kg of the subject's body weight substantially at mealtime. Alternatively, the LNAA supplement can be administered, for example, in multiple oral doses spaced throughout the day (e.g., administered every 2-6 hours). Optionally, the LNAA supplement can be formulated so as to provide sustained release of the LNAAs over a period of time.

The methods of the various aspects of the present invention discussed above can include further steps. Illustratively, the method of the present invention can further include restricting the subject's dietary intake of phenylalanine. For the purposes of the present invention, a subject's dietary intake of phenylalanine is to be deemed to be restricted if the subject's diet (i) is chosen, in whole or in part, on the basis of phenylalanine content or (ii) if the subject's diet contains a total daily phenylalanine intake substantially less (e.g., more than 50% less) than the general population's total daily phenylalanine intake. Alternatively, the method of the present invention can further include not restricting the subject's dietary intake of phenylalanine. For the purposes of the present invention, a subject's dietary intake of phenylalanine is to be deemed to be not restricted if the subject's diet contains a total daily phenylalanine intake that is substantially the same (e.g., plus or minus less than 50%) as the general population's total daily phenylalanine intake.

The present invention, in yet other aspects thereof, relates to the aforementioned LNAA supplements.

Illustratively, the present invention relates to a LNAA supplement which includes Leu and Val and in which the weight ratio of Leu to Val is greater than 2:1.

In another aspect, the present invention relates to a LNAA supplement which includes Leu and iLeu and in which the weight ratio of Leu to iLeu is greater than 3:1.

In yet another aspect, the present invention relates to a LNAA supplement which includes one or more LNAAs and further includes Lys.

In still another aspect, the present invention relates to a LNAA supplement which includes, per 600 mg of LNAA supplement, from about 100 mg to about 290 mg of Tyr; from about 30 mg to about 90 mg of Trp; from about 25 mg to about 75 mg of Met; from about 15 mg to about 45 mg of iLeu; from about 15 mg to about 50 mg of Threo; from about 15 mg to about 50 mg of Val; from about 40 mg to about 200 mg of Leu; from about 15 mg to about 45 mg of His; and from about 15 mg to about 50 mg of Arg.

Examples of the LNAA supplements of the present invention include those described hereinabove with reference to the methods of the present invention. These LNAA supplements can be prepared using amino acids derived from natural sources, or the amino acids can be prepared synthetically by methods well known to those skilled in the art. They can be of any suitable dosage form, such as those discussed above, suitable for enteral administration, and they can contain, in addition to large neutral amino acids and other amino acids, vitamins, minerals, excipients, and the like. For example, suitable dosage forms for oral administration include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. The aforementioned capsules or tablets can, optionally, be formulated to as to provide sustained release of the LNAAs over a period of time. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

The present invention, in yet another aspect thereof, relates to a method for treating a subject suffering from a condition involving a metabolic disorder involving the metabolism of a first amino acid X. The method includes enterally administering to the subject a composition which is substantially free from said first amino acid X and which includes a second amino acid Y that competes with amino acid X at a gastrointestinal tract transporter, such as a Caco-2 cell transporter. As used in this context, a composition is to be deemed to be substantially free from first amino acid X when amino acid X is present in an amount that is less than 10% (e.g., less than about 9%, less than about 8%, less than about 7%, less than about 6%, less than about 5%, less than about 4%, less than about 3%, less than about 2%, and/or less than about 1%), by weight, of the total weight of all of the amino acids present in the composition.

As one skilled in the art will appreciate, the composition used in this aspect of the present invention can further include (i.e., in addition to second amino acid Y) other components, such as other amino acids (e.g., one or more other amino acids which compete with amino acid X at a Caco-2 cell transporter or other gastrointestinal tract transporter). Moreover, as one skilled in the art will appreciate, the method of this aspect of the present invention can further include additional steps, such as administering a second composition which includes, for example, one or more other amino acids (e.g., other than second amino acid Y) which compete with amino acid X at a Caco-2 cell transporter or another gastrointestinal tract transporter.

In one embodiment of this aspect of the present invention, the condition is phenylketonuria and/or phenylalanemia, the first amino acid X is phenylalanine, and the composition is one of the LNAA supplements described hereinabove.

In another embodiment of this aspect of the present invention, the condition is not phenylketonuria and/or phenylalanemia.

In another embodiment of this aspect of the present invention, the condition is tyrosinemia; the first amino acid X is tyrosine; and the second amino acid Y is selected from Phe, Leu, Trp, Lys, His, and combinations thereof.

In yet another embodiment of this aspect of the present invention, the condition is tyrosinemia; the first amino acid X is tyrosine; and the second amino acid Y is selected from Leu, Trp, Lys, His, and combinations thereof.

In still another embodiment of this aspect of the present invention, the condition is alkaptonuria; the first amino acid X is selected from phenylalanine, tyrosine, and combinations thereof; and the second amino acid Y is selected from Leu, Trp, Lys, His, and combinations thereof.

In still another embodiment of this aspect of the present invention, the condition is homocystinuria; wherein the first amino acid X is methionine; and the second amino acid Y is an amino acid that competes with methionine at a gastrointestinal tract transporter.

In still other embodiments of this aspect of the present invention, the condition is a disorder affecting metabolism of a branched amino acid selected from leucine, isoleucine, valine, and combinations thereof; the first amino acid X is selected from leucine, isoleucine, valine, and combinations thereof; and the second amino acid Y is an amino acid that competes with the first amino acid X at a gastrointestinal tract transporter. Such conditions include, for example, maple syrup urine disease, isovaleric acidemia, methylmalonic acidemia, and propionic acidemia.

The method of this aspect of the present invention can be carried out by any suitable form of enteral administration of the composition to the subject. It will be appreciated that the actual preferred amount of composition to be administered according to the present invention will vary according to the particular amino acid or acids that are present in the composition, the nature of the other components present in the composition, and the form of enteral of administration. Many factors that may modify the action of the composition (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests, such as those described in the examples which follow. Briefly, dosing can be based on the plasma level of first amino acid X. For example, dosing can be based on the plasma level of first amino acid X at 0, 3, and/or 6 hours following administration of the composition.

Illustratively, the composition can be administered in a single oral dose of from about 0.1 g to about 10 g per kg of the subject's body weight substantially at mealtime. For example, the composition can be administered in a single oral dose of from about 0.2 g to about 5 g per kg, such as from about 0.3 g to about 3 g per kg, from about 0.4 g to about 2 g per kg, from about 0.5 g to about 1 g per kg of the subject's body weight substantially at mealtime. Alternatively, the composition can be administered, for example, in multiple oral doses spaced throughout the day (e.g., administered every 2-6 hours).

The method this aspect of the present invention can include further steps (i.e., in addition to enteral administration of the composition. Illustratively, the method of the present invention can further include restricting the subject's dietary intake of first amino acid X. For the purposes of the present invention, a subject's dietary intake of first amino acid X is to be deemed to be restricted if the subject's diet (i) is chosen, in whole or in part, on the basis of the amount of first amino acid X present in a particular food or (ii) if the subject's diet contains a total daily intake of first amino acid X that is substantially less (e.g., more than 50% less) than the general population's total daily intake of first amino acid X. Alternatively, the method of the present invention can further include not restricting the subject's dietary intake of first amino acid X. For the purposes of the present invention, a subject's dietary intake of first amino acid X is to be deemed to be not restricted if the subject's diet contains a total daily intake of first amino acid X that is substantially the same (e.g., plus or minus less than 50%) as the general population's total daily intake of first amino acid X.

Compositions useful in the practice of this aspect of the present invention can be prepared using amino acids derived from natural sources, or the amino acids can be prepared synthetically by methods well know to those skilled in the art. The compositions can be of any suitable dosage form, such as those discussed above, suitable for enteral administration, and they can contain, in addition to amino acid Y, other amino acids, vitamins, minerals, excipients, and the like. For example, suitable dosage forms for oral administration include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid;

binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

The present invention is further illustrated with the following examples. In some of the following examples, applicant discusses what is presently believed to be the mechanism by which the present invention operates. This discussion is presented only for the purposes of discussion and is not meant, in any way, to limit the scope of the present invention.

EXAMPLES

Example 1

The Hypothesis

The availability of amino acids in the brain is determined by (i) the plasma supply of the amino acid, and (ii) competition of the plasma-supplied amino acids for a common amino acid binding site(s) on the carrier protein of the BBB neutral amino acid transporter. It has been hypothesized that competition for neutral amino acids at a common carrier binding site, under physiological conditions, is unique to the central nervous system (Pardridge, which is hereby incorporated by reference), and that such competition is the basis for the correlation of BBB transport and clinical disorders affecting the brain (e.g., PKU). Whereas prior PKU-related studies have focused on competitive transport of non-Phe LNAAs across the blood brain barrier so as to suppress entry of Phe into the brain, it has ignored the transport of LNAAs out of the gastrointestinal tract and into the blood, which can be a major determinant of the plasma amino acid supply.

Nine separate transport systems have been identified in the BBB (Oldendorf, "Measurement of Brain Uptake of Radiolabelled Substances Using a Tritiated Water Internal Standard," *Brain Res.*, 24(2):372-376 (1970), which is hereby incorporated by reference). Transport of a given substrate across the BBB is characterized by its affinity constant $K_m$. A lower $K_m$ value corresponds to greater affinity for the binding site of the carrier protein. Each BBB transport system mediates the trans-capillary flux of a group of substrates. For example, one transport system mediates transport of LNAAs, another mediates transfer of hexoses, etc.

Three of the BBB transport systems mediate transport of the common amino acids, with separate carrier proteins for LNAAs, for basic amino acids, and for acidic amino acids. The values of the Michaelis constant, $K_m$, for the three classes of common amino acids are presented below in Table 1 (Pardridge, which is hereby incorporated by reference).

TABLE 1

| system | representative amino acid or other substrate | Km (mM) |
| --- | --- | --- |
| neutral amino acids | Phe | 0.12 |
| basic amino acids | Lys | 0.10 |
| acidic amino acids | Glu | 0.04 |
| hexoses | glucose | 9 |
| thyroid hormone | T3 | 0.0011 |

Although much quantitative information has been obtained on the BBB transport systems, relatively little is known regarding the modulation of the carrier proteins. Developmental or pathological induction or repression of transporter activity would be expected to profoundly influence the pathways of brain metabolism, which are limited by precursor availability.

The absolute and apparent $K_m$ values of the neutral amino acids at the BBB have been determined experimentally (Pardridge, which is hereby incorporated by reference). The absolute value of $K_m$ is the value of $K_m$ in the absence of competition from other neutral amino acids for the binding site on the LNAA carrier protein. The "apparent $K_m$" is the value of $K_m$ in the presence of other LNAAs competing for the binding site on the LNAA carrier protein. The apparent $K_m$ ("$K_m$ (app)") value of a given amino acid is calculated from the absolute $K_m$ value and the sum of the ratios of the plasma level of each LNAA divided by its $K_m$ value, as shown in Equation 1, below.

$$Km(app) = Km(1 + \Sigma[aa]/Km) \quad \text{(Eq. 1)}$$

The experimental values of Km(app) for the LNAA transport system in the BBB are presented below in Table 2 (Pardridge, which is hereby incorporated by reference).

TABLE 2

| amino acid | typical plasma level (mM) | Km (mM) | Km (app) (mM) |
| --- | --- | --- | --- |
| LNAA's | | | |
| Phe | 0.05 | 0.12 | 0.45 |
| Leu | 0.10 | 0.15 | 0.53 |
| Tyr | 0.09 | 0.16 | 0.58 |
| Trp | 0.10 | 0.19 | 0.71 |
| Met | 0.04 | 0.19 | 0.77 |
| iLeu | 0.07 | 0.33 | 1.3 |
| Val | 0.14 | 0.63 | 2.5 |
| Threo | 0.19 | 0.73 | 3.0 |
| Basic aa's | | | |
| His | 0.05 | 0.28 | 1.1 |
| Arg | 0.10 | 0.09 | 0.40 |
| Lys | 0.30 | 0.10 | 0.25 |

Equation 1 predicts that, if the plasma level of an LNAA is much less than its value of $K_m$, then that amino acid will not compete effectively for the carrier protein binding site. The $K_m$ for binding of LNAAs to carrier proteins in organs other than brain is 5-10 mM (see Table 3), which is 50-100 times higher than the physiological plasma concentration of LNAAs. Equation 1 predicts that significant competition effects will not occur under normal physiological conditions in vivo for LNAAs in tissues other than brain. However, competition has been demonstrated in peripheral tissue in vitro at plasma amino acid concentrations of 5-50 M. From these observations, applicant hypothesized that high levels of non-Phe amino acid supplement could conceivably compete with Phe at the GI tract transporter.

Experimental values of $K_m$ for transport in intestinal epithelia are presented below, in Table 3 (Pardridge, which is hereby incorporated by reference).

TABLE 3

| amino acid | intestinal epithelia Km (mM) |
| --- | --- |
| Phe | 1 |
| Leu | 2 |
| Met | 5 |

TABLE 3-continued

| amino acid | intestinal epithelia Km (mM) |
|---|---|
| His | 6 |
| Val | 3 |

Since LNAAs are associated with several clinical disorders, and since the LNAAs enter the brain via the LNAA transporter of the BBB, brain clearance of these amino acids is subject to the effects of the aforementioned competition. Since Phe has a relatively high affinity for the LNAA transporter (Table 1), and since plasma levels of Phe are markedly elevated in phenylketonuria, PKU results in saturation of the BBB carrier protein binding sites by Phe and, hence, excessive levels of Phe in the brain and depressed levels of the other LNAAs in the brain (Pardridge, "Blood-Brain Barrier Carrier-Mediated Transport and Brain Metabolism of Amino Acids," *Neurochem. Res.*, 23:635-644 (1998), which is hereby incorporated by reference).

It was thus hypothesized that non-Phe LNAA supplementation might compete effectively with Phe at the BBB transport system, reducing Phe transport into the brain and increasing transport of the other LNAAs and thus moderating the symptoms of PKU (Andersen et al., "Lowering Brain Phe Levels by Giving Other LNAAs," *Arch. Neurol.*, 33(10):684-686 (1976) and Kaufman, "Phenylketonuria: Biochemical Mechanisms," pp. 1-132 in Agranoff et al., eds, *Advances in Neurochemistry*, New York: Plenum Press (1977), which are hereby incorporated by reference). To reduce influx of Phe into the brain, a supplement of branched chain neutral amino acids comprising valine, isoleucine, and leucine, was administered to older PKU patients (Berry, which is hereby incorporated by reference), who reported significant improvement in behavioral deficits. Kaufman proposed that the addition of the neurotransmitter precursors, tyrosine and tryptophan, to Berry's supplement, should lead to further improvement (Kaufman, which is hereby incorporated by reference).

This hypothesis was tested experimentally by quantitative NMR measurement of brain levels of Phe in PKU patients during Phe oral challenge (0.1 g/kg) with and without supplementation by 0.15 g/kg non-Phe LNAAs (Pietz et al, "Large Neutral Amino Acids Block Phenylalanine Transport into Brain Tissue in Patients with Phenylketonuria," *J. Clin. Invest.*, 103(8):1169-1178 (1999) ("Pietz"), which is hereby incorporated by reference). The LNAA supplement contained valine, methionine, isoleucine, leucine, tyrosine, histidine, and tryptophan. Baseline plasma level of Phe was 1 mM and brain level of Phe was 0.25 mM. Without LNAA supplementation, Pietz, which is hereby incorporated by reference, observed brain Phe increasing to 0.4 mM after Phe challenge, accompanied by disturbed brain activity on an EEG. However, with concurrent LNAA supplementation, Phe influx into the brain was completely blocked, and there was no slowing of EEG activity. These research studies led Nilab to develop Prekunil, a commercial LNAA supplement for treatment of PKU.

Example 2

LNAA Supplement Formulation

As indicated above, the present inventor hypothesized that a LNAA dietary supplement designed to both compete with and suppress transport of Phe from the GI tract into the blood and to compete with and suppress transport of Phe from the blood across the BBB into the brain could be used as a PKU treatment. More particularly, it was hypothesized that oral administration of the LNAA supplement at each meal should suppress Phe transport from the GI tract into the blood so that the BBB transporter system is not overwhelmed by the high levels of Phe typically present in the blood of the PKU patient.

As shown in Equation 1, the term [(aa)/Km] of each amino acid represents that amino acid's ability to compete with Phe at a carrier protein binding site. As seen in Table 1, Leu, Tyr, Trp, and Met are LNAAs which should compete effectively with Phe at the BBB carrier protein.

Although little work has been done in characterizing the affinity of the LNAAs for the binding site of the carrier protein in the GI tract, in vitro measurement of LNAA inhibition of Phe transport in human intestinal epithelial cells (Hidalgo et al., "Transport of a Large Neutral Amino Acid (Phenylalanine) in a Human Intestinal Epithelial Cell Line: Caco-2.," *Biochim. Biophys. Acta*, 1028:25-30 (1990) (Hidalgo"), which is hereby incorporated by reference) indicated that Leu was a strong inhibitor and, interestingly, that LNAAs and basic amino acids appear to share a carrier protein binding site in the intestinal cells, with Lys exhibiting a strong inhibition of Phe transport. Table 4 sets forth the results of experiments to determine the amino acid inhibition of Phe transport in Caco-2 cells in which 10 μM Phe in buffer was applied to monolayers in presence of 1 mM concentration of each amino acid and Phe transport across the monolayer was ratioed to that in the absence of the competing amino acid.

TABLE 4

| Inhibitor | % inhibition |
|---|---|
| LNAAs | |
| Leu | 55% |
| Tyr | 45% |
| Trp | 36% |
| Basic aa's | |
| Lys | 50% |
| His | 33% |

Note that the Km value for Phe at the intestinal cell transport system was measured by Hidalgo, which is hereby incorporated by reference, to be 0.56 mM, close to the value of 1 mM reported in Pardridge, which is hereby incorporated by reference. Note also that the variation in Km between different LNAAs in intestinal epithelia (Table 3) is greater than in BBB. For example, the ratio of Km values for Phe/Leu/Met in intestinal epithelia is 1/2/5, whereas, in BBB, it is 1/1.25/1.58.

The LNAA supplement currently used for PKU treatment is Prekunil, whose composition, based on the amino acid makeup of human milk, is shown in Table 5. Based on the observations of inhibition of Phe transport in Caco-2 cells (Hidalgo, which is hereby incorporated by reference), the inventor of the subject invention designed alternative supplements (also set forth in Table 5 as SuppM1 and SuppM2) in which the Prekunil levels of Leu and Lys were increased significantly. The increase in Leu is believed to further suppress Phe transport from the GI tract into the blood, and from the blood into the brain. The increase in Lys is believed to further suppress Phe transport from the GI tract into the blood.

TABLE 5

| amino acid | Prekunil | | SuppM1 | | SuppM2 | |
|---|---|---|---|---|---|---|
| | (mg) | (mmol) | (mg) | (mmol) | (mg) | (mmol) |
| L-Tyr | 194.1 | 1.07 | 194.1 | 1.07 | 195 | 1.08 |
| L-Trp | 61.1 | 0.30 | 61.1 | 0.30 | 51 | 0.25 |

TABLE 5-continued

|  | Prekunil | | SuppM1 | | SuppM2 | |
| --- | --- | --- | --- | --- | --- | --- |
| amino acid | (mg) | (mmol) | (mg) | (mmol) | (mg) | (mmol) |
| L-Met | 49.7 | 0.33 | 49.7 | 0.33 | 32 | 0.21 |
| L-iLeu | 31.5 | 0.24 | 31.5 | 0.24 | 35 | 0.22 |
| L-Threo | 32.8 | 0.28 | 32.8 | 0.28 | 32 | 0.27 |
| L-Val | 32 | 0.27 | 32 | 0.27 | 35 | 0.30 |
| L-Leu | 30 | 0.24 | 130 | 1.00 | 80 | 0.61 |
| L-His | 31.3 | 0.20 | 31.3 | 0.20 | 20 | 0.13 |
| L-Arg | 34 | 0.20 | 34 | 0.20 | 0 | 0 |
| L-Lys | 0 | 0 | 0 | 0 | 20 | 0.14 |
| Total amino acid | 496.5 | 3.13 | 596.5 | 3.89 | 500 | 3.21 |
| FOM-Km(app) for Phe | | 18.3 | | 23.4 | | 19.95 |

Since the [Σ(aa)/Km of each aa] term of Equation 1 expresses the degree to which each amino acid in a supplement competes with Phe at a given transporter system, and since Km of Phe has been measured at the BBB transport system, a figure of merit for the apparent Km for Phe in the presence of each of the amino acid supplements of Table 5 can be expressed by summing the ratios of the number of mmoles of each amino acid in the supplement divided by its Km. This "figure of merit" (also referred to herein as "FOM") is a first order approximation to the degree to which the supplement can suppress transfer of Phe from plasma into the brain and indicates that the supplements of the subject invention should be 28% (SuppM1) and 9% (SuppM2) more effective in suppressing Phe transport from the plasma into the brain than Prekunil. However, note that the SuppM2 supplement is designed to optimize competition with Phe at the GI tract transporter, with only a small improvement in FOM-Km(app) for competition with Phe at the BBB transporter.

Km values of non-Phe LNAAs at the GI tract transporter system are not known for all the non-Phe LNAAs (Table 3), and, thus, similar competition terms cannot be calculated for the subject invention's supplements. However, under the current hypothesis, the Caco-2 cell data of Hidalgo, which is hereby incorporated by reference, set forth in Table 4, does suggest that Leu and Lys should be effective in suppressing Phe transport out of the GI tract into the blood. Thus, augmentation of a supplement such as Prekunil with additional leucine and lysine, as in the SuppM2 supplement should increase competition with Phe at the GI tract transporter, reducing plasma Phe supply to the BBB.

Example 3

Effect of Prekunil, SuppM1, and SuppM2 on Mouse Plasma Phe Levels

The supplements SuppM1 and SuppM2 were administered to mice with PKU, genotype ENU 2/2 with features of classical PKU, in single oral doses of 0.5 g/kg, and the plasma phenylalanine levels were monitored at 0, 3, 6 and 24 hours post-dose. It should be noted that 0.5 g/kg is a relatively low dose of supplement as Prekunil is typically administered at 1 g/kg. It is known that LNAA supplements typically suppress phenylalanine plasma levels for several hours after ingestion, with the effect then diminishing, such that dosing at each meal may be required. Thus, the 6 hour value of phenylalanine was taken as an indicator of the degree to which phenylalanine accumulation had been suppressed.

Data for a single mouse (P448) not receiving any supplement, a single mouse (P455) dosed with the commercial supplement Prekunil, for a single mouse (P430) dosed with Prekunil boosted with 35 mg Leu, for two mice (P456 and P259) dosed with Prekunil plus 100 mg Leu (i.e., SuppM1), and on two mice (P433 and P482) dosed with the SuppM2 supplement are shown in Table 6, below. More particularly, Table 6 shows the Plasma Phe levels (mg/dl) in mice administered LNAA supplements (0.5 g/kg, single dose) at 0, 3, 6, and 24 hours post-dose.

TABLE 6

| Time (hours) | Control P448 | Prekunil P455 | Prekunil + 35 mg Leu P430 | Prekunil + 100 mg Leu (SuppM1) | | SuppM1 | |
| --- | --- | --- | --- | --- | --- | --- | --- |
| | | | | P456 | P259 | P433 | P482 |
| 0 | 33.20 | 27.14 | 27.23 | 25.37 | 27.22 | 18.69 | 21.10 |
| 3 | 30.91 | 24.23 | 26.02 | 23.20 | 25.57 | 14.63 | 16.86 |
| 6 | 28.91 | 22.17 | 25.21 | 17.49 | 19.02 | 13.68 | 15.39 |
| 24 | 30.14 | 20.89 | 27.13 | 20.88 | 21.42 | 20.06 | 23.78 |

Boosting the Prekunil supplement with 100 mg Leu (SuppM1), an amino acid which should compete effectively with Phe at the binding sites of carrier proteins of both the intestinal epithelia and the BBB, thus effected a significant suppression of Phe plasma level. Whereas Prekunil itself effected a 20% reduction in Phe, the SuppM1 supplement effected a 30% reduction in plasma Phe at 6 hours post-dose, for both mice tested. Boosting the supplement with both leucine and lysine to target the GI transporter, as in SuppM2, effected a 70% reduction in plasma Phe at 6 hours post-dose, for both mice tested. The excellent Phe suppression of the SuppM2 supplement is indicative of its capacity to compete more effectively with Phe transport at the GI transporter than the other supplements, while maintaining the ability to compete similarly at the BBB transporter.

Plasma tyrosine analysis for the mice administered SuppM2 indicated stable levels of 0.58-0.50 mg/dl and 0.44-0.40 mg/dl tyrosine over the 24 hour experiment, for mice P433 and P482 respectively.

It will be appreciated that SuppM1 and SuppM2 may not represent optimal LNAA supplement compositions for the treatment of PKU. For example, the LNAA supplements can be modified so as to maintain required brain levels of neurotransmitter precursor amino acids such as tyrosine and tryptophan, while improving competition of the supplement with Phe at the GI tract transporter, and maintaining competition of the supplement with Phe at the BBB transporter.

Example 4

Additional LNAA Supplement Formulation

An additional supplement formulation, dubbed SuppM3 is set forth in Table 7. This supplement formulation further illustrates the compositions and methods of the present invention.

TABLE 7

| amino acid | SuppM3 (mg) |
| --- | --- |
| L-Tyr | 195.0 |
| L-Trp | 51.0 |
| L-Met | 32.0 |
| L-iLeu | 35.0 |
| L-Threo | 32.0 |

TABLE 7-continued

| amino acid | SuppM3 (mg) |
|---|---|
| L-Val | 35.0 |
| L-Leu | 130.0 |
| L-His | 30.0 |
| L-Arg | 30.0 |
| L-Lys | 30.0 |
| Total amino acid | 600.0 |

Although preferred embodiments have been depicted and described in detail herein, it will be apparent to those skilled in the relevant art that various modifications, additions, substitutions and the like can be made without departing from the spirit of the invention, and these are therefore considered to be within the scope of the invention as defined in the claims which follow.

What is claimed:

1. A method for treating a subject suffering from phenylketonuria or phenylalanemia, said method comprising:
   enterally administering to the subject a composition comprising a mixture of amino acids selected from leucine (Leu), lysine (Lys), tyrosine (Tyr), tryptophan (Trp), methionine (Met), isoleucine (Ile), valine (Val), histidine (His), arginine (Arg), and threonine (Thr),
      where the amount of Leu in said mixture is at least 16% by weight of the selected amino acids; and the amount of Lys in said mixture is 2 to 4% by weight of the selected amino acids; and
   b) inhibiting Phe transport from the gastrointestinal tract into the blood by said administering, thereby treating the subject's phenylketonuria or phenylalanemia.

2. A method for treating a subject suffering from phenylketonuria or phenylalanemia, said method comprising:
   enterally administering to the subject a composition comprising a mixture of amino acids selected from Leu, Lys, Tyr, Trp, Met, Ile, Val, His, Arg Thr,
      where the amount of Leu in said mixture is at least 16% by weight of the selected amino acids: and the weight ratio of Leu to Ile in said mixture is at least 3:1; and
   b) inhibiting Phe transport from the gastrointestinal tract into the blood by said administering, thereby treating the subject's phenylketonuria or phenylalanemia.

3. A method for treating a subject suffering from phenylketonuria or phenylalanemia, said method comprising:
   a) enterally administering to the subject a composition comprising a mixture of amino acids selected from Leu, Lys, Tyr, Trp, Met, Ile, Val, His, Arg, and Thr,
      where the amount of Lou in said mixture is at least 16% by weight of the selected amino acids and the weight ratio of Leu to Lys in said mixture is at least 4:1;
   b) inhibiting Phe transport from the gastrointestinal tract into the blood by said administering, thereby treating the subject's phenylketonuria or phenylalanemia.

4. The method of claim 2, where the amount of Lys in said mixture is 2 to 6% Lys by weight of the selected amino acids.

5. The method of claim 3, where the amount of Lys in said mixture is 2 to about 6% Lys by weight of the selected amino acids.

6. The method of claim 1, wherein the weight ratio of Leu to Val in said mixture is at least about 2:1 Leu to Val.

7. The method of claim 4, wherein the weight ratio of Leu to Lys in said mixture is at least 4:1 Leu to Lys.

8. The method of claim 1, where the amount of Tyr, Thr, His, Trp, Met, and Arg in said mixture by weight of the selected amino acids is:
   i) at least 20% Tyr;
   ii) 2.5 to 10% Thr;
   iii) 2.5 to 7.5% His;
   iv) 5 to 15% Trp;
   v) 3 to 10% Met; and
   vi) 0 to 8.3% Arg.

9. The method of claim 2, where the amount of Tyr, Thr, His, Met, Trp, and Arg in said mixture by weight of the selected amino acids is:
   i) at least 20% Tyr;
   ii) 2.5 to 10% % Thr;
   iii) 2.5 to 7.5% % His;
   iv) 5 to 15% Trp;
   vi) 3 to 10% Met; and
   vii) 0 to 8.3% Arg.

10. The method claim 3, where the amount of Tyr, Thr, His, Met, Trp, and Arg in said mixture by weight of the selected amino acids is:
   i) at least 20% Tyr:
   ii) 3 to 8% Thr:
   iii) 3 to 8% His;
   iv) 5 to 15% Trp;
   v) 3 to 10% Met; and
   vi) 0 to 8% Arg.

11. The method of claim 2, where the composition is administered in a dose of 500 to 1000 mg of said amino acid mixture per kg of the subject's body weight.

12. The method of claim 9, where the amount of each amino acid in 500 mg of said mixture of amino acids is:
   100 mg to 290 mg of Tyr;
   25 mg to 75 mg of Trp;
   15 mg to 50 mg of Met;
   15 mg to 55 mg of Ile;
   15 mg to 50 mg of Thr;
   15 mg to 55 mg of Val;
   80 mg 200 mg of Leu;
   10 mg to 30 mg of His; and
   5 mg to 200 mg of Lys.

13. The method of claim 9, where the amount of each amino acid in 600 mg of said mixture of amino acids is:
   100 mg to 290 mg, of Tyr;
   30 mg to 90 mg of Trp;
   25 mg to 75 mg of Met;
   15 mg to 45 mg of Ile;
   15 mg to 50 mg of Thr;
   15 mg to 50 mg of Val;
   130 mg to 200 mg of Leu;
   15 mg to 45 mg of His;
   15 mg to 50 mg of Arg; and
   5 mg to 200 mg of Lys.

14. The method of claim 13, wherein the amount of Lys is 10 mg to 30 mg per 600 mg.

15. The method of claim 1, wherein the composition is administered in a dose of 100 to 2000 mg of said amino acid mixture per kg of the subject's body weight per day.

16. The method of claim 2, wherein the composition is administered in a dose of 100 to 2000 mg of said amino acid mixture per kg of the subject's body weight per day.

17. The method of claim 3, wherein the composition is administered in a dose of 100 to 2000 mg of said amino acid mixture per kg of the subject's body weight per day.

18. The method of claim 1, wherein the composition is administered in a dose of 200 to 1000 mg of said amino acid mixture per kg of the subject's body weight per day.

19. The method of claim 2, wherein the composition is administered in a dose of 200 to 1000 mg of said amino acid mixture per kg of the subject's body weight per day.

20. The method of claim 3, wherein the composition is administered in a dose of 200 to 1000 mg of said amino acid mixture per kg of the subject's body weight per day.

21. The method of claim 1, wherein the composition further contains vitamins, minerals, or excipients.

22. The method of claim 2, wherein the composition further contains vitamins, minerals, or excipients.

23. The method of claim 3, wherein the composition further contains vitamins, minerals, or excipients.

24. The method of claim 1, wherein the composition is in a dosage form is selected from coated or non-coated tablets, dispersible powders, granules, capsules, suspensions, syrups, and elixirs, and sustained release formulations thereof.

25. The method of claim 2, wherein the composition is in a dosage form is selected from coated or non-coated tablets, dispersible powders, granules, capsules, suspensions, syrups, and elixirs, and sustained release formulations thereof.

26. The method of claim 3, wherein the composition is in a dosage form is selected from coated or non-coated tablets, dispersible powders, granules, capsules, suspensions, syrups, and elixirs, and sustained release formulations thereof.

\* \* \* \* \*